United States Patent
Russak

(10) Patent No.: US 9,817,943 B2
(45) Date of Patent: Nov. 14, 2017

(54) CUMULATIVE DIFFERENTIAL CHEMICAL ASSAY IDENTIFICATION

(71) Applicant: AZURE VAULT LTD, Ramat-Gan (IL)

(72) Inventor: Ze'ev Russak, Ramat Gan (IL)

(73) Assignee: AZURE VAULT LTD, Ramat-Gan (IL)

( * ) Notice: Subject to any disclaimer, the term of this patent is extended or adjusted under 35 U.S.C. 154(b) by 0 days.

(21) Appl. No.: 13/988,904

(22) PCT Filed: Oct. 11, 2012

(86) PCT No.: PCT/IB2012/055517
§ 371 (c)(1),
(2) Date: May 22, 2013

(87) PCT Pub. No.: WO2013/054288
PCT Pub. Date: Apr. 18, 2013

(65) Prior Publication Data
US 2015/0112608 A1    Apr. 23, 2015

Related U.S. Application Data

(63) Continuation of application No. 13/273,277, filed on Oct. 14, 2011.

(51) Int. Cl.
*G01N 31/00* (2006.01)
*G06F 19/20* (2011.01)
(Continued)

(52) U.S. Cl.
CPC ............ *G06F 19/20* (2013.01); *C12Q 1/686* (2013.01); *C12Q 1/6816* (2013.01);
(Continued)

(58) Field of Classification Search
CPC ........ G06F 19/20; G01N 21/64; C12Q 1/6851
(Continued)

(56) References Cited

U.S. PATENT DOCUMENTS

| 6,503,720 B2 | 1/2003 | Wittwer et al. |
| 6,783,934 B1 * | 8/2004 | McMillan ............ C12Q 1/6851 435/287.2 |

(Continued)

FOREIGN PATENT DOCUMENTS

| WO | 03029924 A2 | 4/2003 |
| WO | 2005030990 A1 | 4/2005 |

(Continued)

OTHER PUBLICATIONS

Nellaker et al., Molecular Beacon-Based Temperature Control and Automated Analyses for Improved Resolution of Melting Temperature Analysis Using SYBR I Green Chemistry. Clin Chem. Jan. 2007;53(1):98-103.
(Continued)

*Primary Examiner* — Stephanie Bloss
(74) *Attorney, Agent, or Firm* — Acuity Law Group, PC; Michael A. Whittaker

(57) ABSTRACT

An apparatus comprising: a value receiver, configured to receive fluorescence values measured during a chemical reaction involving a test sample, each value pertaining to a respective physical parameter value, a difference calculator, configured to calculate differences, each difference being between respective one of the measured fluorescence values and one of reference fluorescence values of a reference sample, each reference fluorescence value pertaining to a respective physical parameter value, a cumulative index calculator, configured to calculate a cumulative index, by selecting a first difference among the calculated differences, and selecting and adding to the first difference differences, each one of the added differences being selected according to a proximity standard applied on each two differences selected in a sequence, the proximity standard being based on proximity of physical parameter values and difference size, and a similarity determiner, configured to determine
(Continued)

similarity between the samples, using the calculated cumulative index.

18 Claims, 8 Drawing Sheets

(51) Int. Cl.
  *G01N 21/64* (2006.01)
  *G06F 19/00* (2011.01)
  *C12Q 1/68* (2006.01)
(52) U.S. Cl.
  CPC ........... *C12Q 1/6851* (2013.01); *G01N 21/64* (2013.01); *G01N 21/6428* (2013.01); *G06F 19/702* (2013.01)
(58) Field of Classification Search
  USPC .......................................................... 702/22
  See application file for complete search history.

(56) References Cited

U.S. PATENT DOCUMENTS

| | | | |
|---|---|---|---|
| 6,911,327 | B2 | 6/2005 | McMillan et al. |
| 6,990,459 | B2 | 1/2006 | Schneider |
| 8,282,455 | B2 | 10/2012 | Kelly, Jr. et al. |
| 8,442,707 | B2 | 5/2013 | Ledesma et al. |
| 2006/0224330 | A1 | 10/2006 | Kurnik et al. |
| 2007/0073489 | A1 | 3/2007 | Kurnik et al. |
| 2007/0073490 | A1 | 3/2007 | Kurnik et al. |
| 2007/0124088 | A1 | 5/2007 | Woo et al. |
| 2007/0129899 | A1 | 6/2007 | Ward et al. |
| 2007/0148632 | A1 | 6/2007 | Kurnik et al. |
| 2009/0119020 | A1 | 5/2009 | Kurnik et al. |
| 2009/0222503 | A1* | 9/2009 | Palais .................. C12Q 1/6816 708/277 |

FOREIGN PATENT DOCUMENTS

| | | |
|---|---|---|
| WO | 2011/019837 A1 | 2/2011 |
| WO | 2011019837 A1 | 2/2011 |
| WO | 2011/030186 A1 | 3/2011 |

OTHER PUBLICATIONS

Hartshorn et al., One-Step RT-LATE-PCR for mRNA and Viral RNA Detection and Quantification, RT-PCT Protocols: Second Edition, Methods in Biology, vol. 630, pp. 153-185, 2010.
International Search Report and Written Opinion dated Feb. 27, 2013 in international application No. PCT/IB2012/055517.
Brechtbuehl et al., A rapid real-time quantitative polymerase chain reaction for hepatitis B virus. J Virol Methods. Apr. 2001;93(1-2):105-113.
Hartshorn and Wang H, One-Step RT-LATE-PCR for mRNA and Viral RNA Detection and Quantification. Methods Mol Biol. 2010;630:153-185.
Lee et al., ResonSense: simple linear fluorescent probes for quantitative homogenous rapid polymerase chain reaction. Analytica Chimica Acta 2002,;457:61-70.
Sanchez et. al., Linear-After-The-Exponential (LATE)—PCR: An advanced method of asymmetric PCR and its uses in quantitative real-time analysis, Proc Natl Acad Sci U S A. Feb. 17, 2004;101(7):1933-1938.
Notice on Intention to Grant a European Patent on the European Patent Application No. 12 839 887.2 corresponding the instant application, issued by the European Patent Office (EPO) on Mar. 30, 2016.
Biedermann et al., Comparison of Real-Time PCR Signal-Amplified in Situ Hybridization and Conventional PCR for Detection and Quantification of Human Papillomavirus in Archival Cervical Cancer Tissue. J Clin Microbiol. Aug. 2004; 42(8): 3758-3765.

* cited by examiner

CUMULATIVE DIFFERENTIAL CHEMICAL ASSAY IDENTIFICATION

FIELD AND BACKGROUND OF THE INVENTION

The present invention relates to analyzing chemical assays and, more particularly, but not exclusively to cumulative differential photometric chemical assay identification.

Some chemical assays can be identified by monitoring their varying photometric properties in an ongoing chemical reaction (say in an on going Quantitative Fluorescent Polymerase Chain Reaction (QF-PCR), on a DNA (Deoxyribonucleic acid) Melting Reaction, or in another chemical reaction), as known in the art.

More specifically, crucial decisions in pre-implantation genetic diagnosis, infectious diseases, bioterrorism, forensics, and cancer research have increasingly depended on identification of specific DNA sequences, even down to alleles of single-copy genes in single cells.

The identification typically involves introduction of fluorescently active agents that emit or quench fluorescent light when connected in a weak bond, say to a specific DNA sequence, when disconnected from the weak bond, etc.

Melting Curve Analysis is often used, to map the hybridization temperature of two complementary DNA strands, or of a single DNA strand to a fluorescence emitting (or fluorescence quenching) sequence specific hybridizing probes (i.e. sequence specific fluorescently active agents).

The temperature may depend on the energy required to break base-base hydrogen bonding between two strands of DNA.

The energy is dependent on the strand's length, GC (Guanine-Cytosine) content, complementarity, etc.

PCR methods that monitor DNA melting with sequence specific fluorescently active agents have become popular in conjunction with real-time PCR. Because PCR produces enough DNA for fluorescent melting analysis, both amplification and analysis can be performed in a same reaction tube, thus providing a homogeneous, closed-tube system that requires no processing or separation steps.

In implementation, the tube is heated and photometers are used to measure fluorescent light in the reaction tube as a function of temperature. The fluorescent light in the reaction tube may also be measured post heating, as the temperature in the reaction tube gradually declines.

Conventional real-time PCR may permit rapid and quantitative identification of unique DNA targets (i.e. specific DNA sequences) on a double stranded DNA, but reactions typically slow down and plateau stochastically because re-annealing of the DNA's strands gradually outcompetes primer and probe binding to the strands, as know in the art.

Asymmetric PCR preferentially amplifies one strand of DNA. Asymmetric PCR potentially circumvents the problem of strand re-annealing, by using unequal primer concentrations. Depletion of the limiting primer during the exponential amplification of the PCR reaction results in linear synthesis of strands extended from the excess primer.

Although asymmetric PCR generates brighter signals than symmetric PCR does, asymmetric PCR is seldom used because it is much less efficient than conventional PCR, as described in further detail hereinbelow. Asymmetric PCR also requires extensive optimization to identify the proper primer ratios, the amounts of starting material, and the number of amplification cycles that can generate reasonable amounts of product for specific DNA sequences.

LATE (Linear after the exponential) PCR is a recently introduced technique.

LATE PCR was described by J. Aquiles Sanchez, Kenneth E. Pierce, John E. Rice, and Lawrence J. Wangh of the Biology Department of the Brandeis University, in an article published in PNAS (Proceedings of the National Academy of Sciences of the US), on Feb. 17, 2004, in Vol. 101, No. 7, on pages 1933-1938, entitled: "Linear-After-The-Exponential (LATE) PCR: An advanced method of asymmetric PCR and its uses in quantitative real-time analysis".

While conventional symmetric PCR typically uses equimolar concentrations of two primers with similar melting points, conventional asymmetric PCR assays are inefficient and unpredictable, because they are designed using symmetric primers, without taking into account the effect of the actual primer concentrations on primer melting points.

LATE-PCR provides a rational approach to generating single-stranded DNA products based on knowledge of the primer-target hybridization equilibriums that drive asymmetric reactions. As a result, LATE-PCR may exhibit similar efficiency to symmetric PCR and enable the use of primers over a wide range of concentration ratios.

Under LATE-PCR conditions, the initial exponential phase of the reaction generates double-stranded amplicons until the limiting primer concentration falls abruptly and the reaction switches to synthesis of only excess primer strands.

In the case of real-time LATE-PCR, the amount of limiting primer is deliberately chosen such that the exponential phase of the reaction switches to the linear phase shortly after the reaction reaches detectability, i.e., at the $C_T$ value.

LATE-PCR therefore maintains the quantitative nature of real-time symmetric PCR assays, which is based on the $C_T$ values of the exponential phase of the reaction. Upon switching, the number of excess primer strands accumulated per cycle is proportional to the number of limiting primer strands present at the time of the switch.

LATE-PCR makes it possible to introduce a detection step distinct from the annealing step. The temperature of the detection, therefore, can be lowered to permit the use of low melting temperature probes with a greater allele-discrimination capacity and an improved signal-to-noise ratio.

Because the melting temperature of a low-melting temperature probe is well below the extension temperature of the reaction, saturating concentrations can be used to detect all of the single-stranded molecules produced.

The classification of chemical assays using any one of the above described methods includes a final step, in which an expert in the field manually examines a graph which represents fluorescence light measured through the chemical reaction, as a function of a physical parameter such as temperature.

The expert may further compare the examined graph with reference graphs, say for identifying occurrence of certain DNA sequences (say certain mutations), as known in the art.

SUMMARY OF THE INVENTION

According to one aspect of the present invention, there is provided an apparatus for cumulative differential chemical assay identification. The apparatus comprises: a value receiver, configured to receive a plurality of fluorescence values measured during a chemical reaction involving a test sample, each one of the fluorescence values pertaining to a respective one of a first series of physical parameter values, and a difference calculator, in communicated with the value receiver, configured to calculate a plurality of pairwise differences, each difference being between a respective one of the measured fluorescence values and a respective one of reference fluorescence values of a reference sample, each one of the reference fluorescence values pertaining to a respective one of a second series of physical parameter values.

The apparatus further comprises a cumulative index calculator, in communicated with the difference calculator, configured to calculate a cumulative index, by selecting a first difference among the calculated pairwise differences, and selecting and adding to the first difference a plurality of ones of the pairwise differences, each one of the added differences being selected according to a proximity standard applied on each two differences selected in a sequence, the proximity standard being based on proximity of physical parameter values and on difference size, and a similarity determiner, in communicated with the cumulative index calculator, configured to determine similarity between the test sample and the reference sample, using the calculated cumulative index.

According to a second aspect of the present invention, there is provided a method for cumulative differential chemical assay identification.

The method comprises receiving a plurality of fluorescence values measured during a chemical reaction involving a test sample, each one of the fluorescence values pertaining to a respective one of a first series of physical parameter values, and calculating a plurality of pairwise differences, each difference being between a respective one of the measured fluorescence values and a respective one of reference fluorescence values of a reference sample, each one of the reference fluorescence values pertaining to a respective one of a second series of physical parameter values.

The method further comprises calculating a cumulative index, by selecting a first difference among the calculated pairwise differences, and selecting and adding to the first difference a plurality of ones of the pairwise differences, each one of the added differences being selected according to a proximity standard applied on each two differences selected in a sequence, the proximity standard being based on proximity of physical parameter values and on difference size, and determining similarity between the test sample and the reference sample, using the calculated cumulative index.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

Moreover, according to actual instrumentation and equipment of preferred embodiments of the method and system of the present invention, several selected steps could be implemented by hardware or by software on any operating system of any firmware or a combination thereof.

For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings.

With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings:

FIG. 1 is a block diagram schematically illustrating an apparatus for cumulative differential chemical assay identification, according to an exemplary embodiment of the present invention.

FIG. 2 is a simplified flowchart schematically illustrating a first method for cumulative differential chemical assay identification, according to an exemplary embodiment of the present invention.

FIG. 3 is a simplified diagram schematically illustrating an exemplary proximity standard, according to an exemplary embodiment of the present invention.

FIG. 4 is a simplified diagram schematically illustrating summing of differences, according to an exemplary embodiment of the present invention.

FIG. 5A is a first simplified diagram schematically illustrating summing of differences within predefined boundaries, according to an exemplary embodiment of the present invention.

FIG. 5B is a second simplified diagram schematically illustrating summing of differences within predefined boundaries, according to an exemplary embodiment of the present invention.

FIG. 6 is a simplified flowchart schematically illustrating a second method for cumulative differential chemical assay identification, according to an exemplary embodiment of the present invention.

FIG. 7 is a simplified flowchart schematically illustrating a third method for cumulative differential chemical assay identification, according to an exemplary embodiment of the present invention.

FIG. 8 is a simplified flowchart schematically illustrating a fourth method for cumulative differential chemical assay identification, according to an exemplary embodiment of the present invention.

DESCRIPTION OF THE PREFERRED EMBODIMENTS

Figure 1:
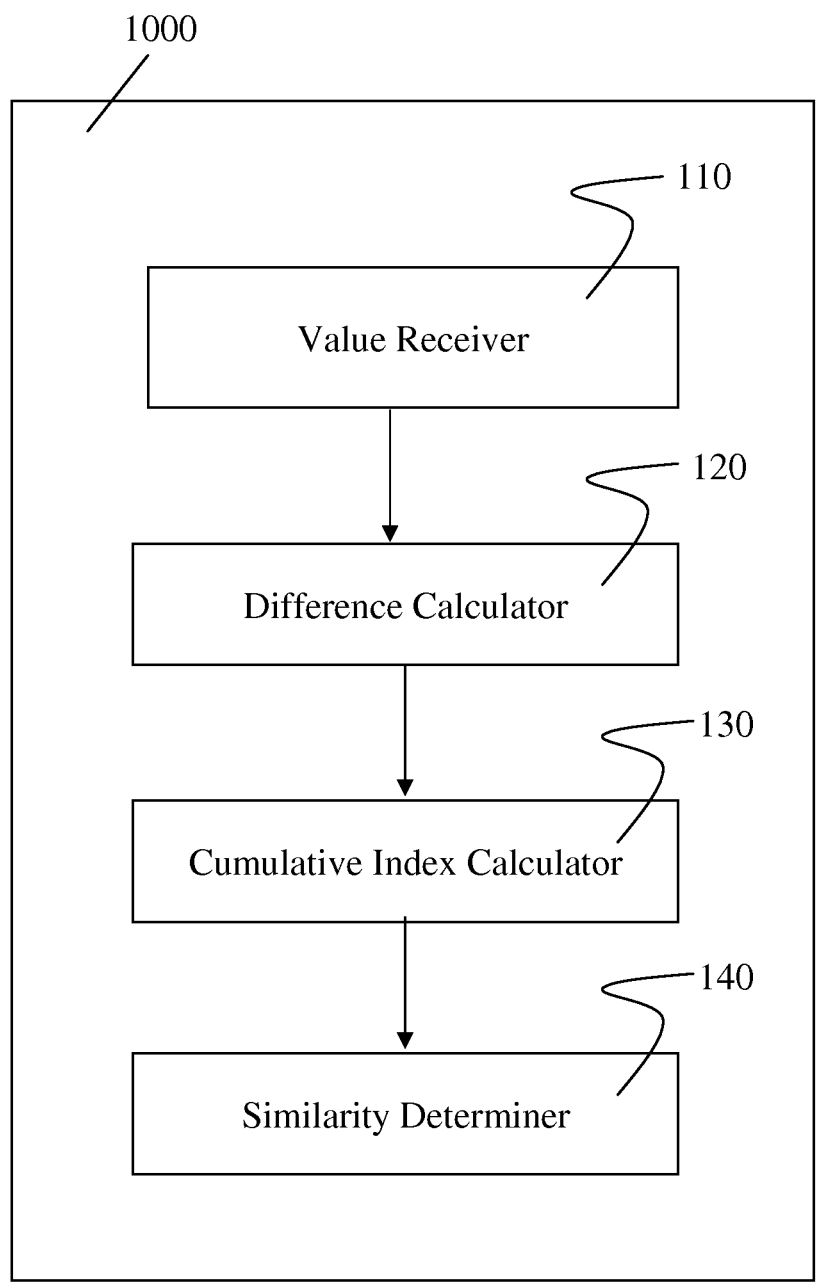

The present embodiments comprise methods and apparatuses for cumulative differential chemical assay identification.

Currently, comparisons made between fluorescence values measured during a chemical reaction (say LATE-PCR) which involves a test sample, and reference fluorescence values of a similar chemical reaction which involves a reference sample (typically of known content), often serve for identification of the test sample, as described in further detail hereinabove.

However, the currently serving comparisons are based on a pre-assumption that samples of similar content such as similar DNA sequences (say samples bearing a same mutation in a microorganism's DNA) yield similar fluorescence values for similar respective physical parameter values (say for a same temperature or pressure).

Consequently, the identification is typically based on calculation of differences between pairs of fluorescence values. Each pair pertains to a same value of the physical parameter, say a same temperature or pressure.

However, sensor variation, electrical noise, different ion compositions of analytes, delayed responses by a controller or a processor, and other factors, may introduce distortions into the measured fluorescence values. Consequently, similar fluorescence values may be somewhat distanced. That is to say that the similar fluorescence values may appear for different values of the physical parameter (i.e. in displacement) rather than for a very same value of the physical parameter.

The currently serving comparisons may thus yield inaccurate results when such distortions are present in the measured values.

An exemplary method, according to an exemplary embodiment of the present invention, may help overcome the distortions.

In the exemplary method, there are received fluorescence values. The fluorescence values are values measured during a chemical reaction (say QF-PCR) which involves a test sample. Each one of the measured fluorescence values pertains to a respective one of a first series of physical parameter values (say to a specific temperature present in a reaction chamber in which the chemical reaction occurs, when the fluorescence value is measured).

Then, there are calculated pairwise differences. Each calculated difference is a difference between a respective one of the measured fluorescence values and a respective one of reference fluorescence values of a reference sample. Each one of the reference fluorescence values pertains to a respective one of a second series of physical parameter values.

The difference may an absolute difference calculated by subtracting the measured fluorescence value from the reference fluorescence value (or vise versa), a geometrical distance between points that represent the two fluorescence values, or a difference calculated using a specific user defined formula, as described in further detail hereinbelow.

Preferably, the two series of physical parameter values are identical. That is to say that for each one of the measured fluorescence values, there exists a reference fluorescence value which pertains to a same physical parameter value, say to a same temperature, pressure, etc.

In one example, the calculated differences include all possible differences between a respective one of the measured fluorescence values and a respective one of the reference fluorescence values. That is to say that if there are n measured fluorescence values for respective n physical parameter values, and m reference fluorescence values for respective m physical parameter values, then, there are calculated m×n differences.

In another example, only some of the m×n differences are calculated (say only differences each of which is a difference between a reference fluorescence value and a measured fluorescence value that pertain to values of the physical parameter within a predefined difference from each other, etc.), as described in further detail hereinbelow.

In the exemplary method, there is calculated a cumulative index, by summing differences selected amongst the calculated pairwise differences. The differences are selected amongst the calculated pairwise differences, according to a proximity standard applied on each two differences selected in a sequence (i.e. one after the other), as described in further detail hereinbelow.

Finally, there is determined similarity between the test sample and the reference sample, using the calculated cumulative index.

The principles and operation of an apparatus and a method, according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1, which is a simplified block diagram schematically illustrating an apparatus for cumulative differential chemical assay identification, according to an exemplary embodiment of the present invention.

An exemplary apparatus 1000 may be implemented as a computer program, as hardware, as a combination of a computer program and hardware, etc.

The exemplary apparatus 1000 for cumulative differential chemical assay identification, according to an exemplary embodiment of the present invention, includes a value receiver 110.

The value receiver 110 receives two or more fluorescence values measured during a chemical reaction (say PCR) which involves a test sample, say a blood sample taken from a patient infected with a bacteria (or a virus) which needs to be identified.

Each one of the fluorescence values pertains to a respective one of a first series of physical parameter values (say to a specific temperature present in a PCR reaction chamber in which the chemical reaction occurs, when the specific fluorescence value is measured).

In one example, the fluorescence values are measured (say by a photometer), during a LATE-PCR reaction, during a DNA Melting process, or during another reaction, run in a reaction chamber, as known in the art.

In the example, each specific one of the measured fluorescence values pertains to a respective temperature measured in the reaction chamber when the specific fluorescence value is measured in the chamber.

The apparatus 1000 further includes a difference calculator 120, in communicated with the value receiver 110.

The difference calculator 120 calculates two or more pairwise differences.

Each calculated difference is a difference between a respective one of the measured fluorescence values and a respective one of reference fluorescence values of a reference sample (say of a sample of known bacterial content, a virus known to bear a specific mutation, etc).

Optionally, the reference fluorescence values are values measured during a previous run of the chemical reaction, which involves the reference sample, values known in the art and available from scientific databases or textbooks, values gathered in previous runs of the chemical reaction on samples known to contain a certain bacteria, etc.

Optionally, the reference sample is a calculated average sample. That is to say that each one of the reference fluorescence values is an average value calculated over fluorescence values measured in previous runs of the chemical reaction, for a same respective physical parameter value (say for a same temperature or pressure).

Each one of the reference fluorescence values pertains to a respective one of a second series of physical parameter values (say a specific temperature of the previous run of the reaction, a specific temperature in a textbook table which lists reference fluorescence values per temperature values, etc).

Preferably, the two series of physical parameter values are identical. That is to say that for each one of the measured fluorescence values, there exists a reference fluorescence value which pertains to a same physical parameter value.

The difference may be an absolute difference calculated by subtracting the measured fluorescence value from the reference fluorescence value (or vise versa), a geometrical distance between points that represent the two fluorescence values, or a difference calculated using a specific formula, say a formula predefined by a user of the apparatus 1000, etc., as known in the art.

Optionally, the calculated pairwise differences include all possible differences, and each of the differences is a difference between a respective one of the measured fluorescence values and a respective one of the reference fluorescence values. That is to say that if there are n measured fluorescence values for respective n physical parameter values, and m reference fluorescence values for respective m physical parameter values, then, there are calculated m×n differences.

Alternatively, the number of differences is limited according to a predefined criterion, and is thus lower than m×n.

In a first example, the criterion is that each of the calculated pairwise differences is a difference between a reference fluorescence value and a measured fluorescence value that pertain to values of the physical parameter within a predefined difference from each other, as described in further detail hereinbelow.

In a second example, the criterion is that each of the calculated pairwise differences is a difference between a reference fluorescence value and a measured fluorescence value within a predefined difference from each other, as described in further detail hereinbelow.

In a third example, the criterion is that each of the calculated pairwise differences is a difference between a reference fluorescence value and a measured fluorescence value of a proportion within a predefined limit. That is to say that the ratio of the two fluorescence values is below a predefined limit, as described in further detail hereinbelow.

The apparatus 1000 further includes a cumulative index calculator 130, in communicated with the difference calculator 120.

The cumulative index calculator 130 calculates a cumulative index, by selecting a first difference among the calculated pairwise differences, and selecting and adding to the first difference two or more additional ones of the pairwise differences, thereby summing the selected differences.

The cumulative index calculator 130 selects each one of the additional differences, according to a proximity standard applied on each two differences selected in a sequence (i.e. one after the other), as described in further detail hereinbelow.

The proximity standard is based on proximity of physical parameter values and on difference size, as described in further detail hereinbelow.

The apparatus 1000 further includes a similarity determiner 140, in communicated with the cumulative index calculator 130, The similarity determiner 140 determines similarity between the test sample and the reference sample, using the calculated cumulative index.

In one example, the similarity determiner 140 may determine that the two samples carry a similar genetic mutation when the calculated cumulative index is below a threshold predefined by a user of apparatus 1000, and that the two samples do not carry the same mutation when the index exceeds the predefined threshold.

In another example, the similarity determiner 140 may determine that the two samples belong to a same class of samples, thus classifying the two samples into a common class.

In a first example, the proximity standard used by the cumulative index calculator 130 is that each selected difference added to the first difference is smallest in a respective group, as described in further detail hereinbelow.

The group consists of calculated ones of the following differences:

1) a difference between a measured fluorescence value which pertains to a highest among the physical parameter values of the first series lower than a physical parameter value to which a measured fluorescence value of a difference selected immediately before the added selected difference pertains, and a reference fluorescence value which pertains to a highest among the physical parameter values of the second series lower than a physical parameter value to which a reference fluorescence value of the difference selected immediately before pertains;

2) a difference between a measured fluorescence value which pertains to the highest among the physical parameter values of the first series lower than the physical parameter value to which the measured fluorescence value of the difference selected immediately before pertains, and a reference fluorescence value which pertains to the physical parameter value to which the reference fluorescence value of the difference selected immediately before pertains; and 3) a difference between a measured fluorescence value which pertains to the physical parameter value to which the measured fluorescence value of the difference selected immediately before pertains, and a reference fluorescence value which pertains to the highest among the physical parameter values of the second series lower than the physical parameter value to which the reference fluorescence value of the difference selected immediately before pertains.

In a second example, the proximity standard used by the cumulative index calculator 130 remains that each selected difference added to the first difference is smallest in a respective group.

However, the group rather consists of calculated ones of the following differences:

1) a difference between a measured fluorescence value which pertains to a lowest among the physical parameter values of the first series higher than a physical parameter value to which a measured fluorescence value of a difference selected immediately before the added selected difference pertains, and a reference fluorescence value which pertains to a lowest among the physical parameter values of the second series higher than a physical parameter value to which a reference fluorescence value of the difference selected immediately before pertains;

2) a difference between a measured fluorescence value which pertains to the lowest among the physical parameter values of the first series higher than the physical parameter value to which the measured fluorescence value of the difference selected immediately before pertains, and a reference fluorescence value which pertains to the physical parameter value to which the reference fluorescence value of the difference selected immediately before pertains; and 3) a difference between a measured fluorescence value which pertains to the physical parameter value to which the measured fluorescence value of the difference selected immediately before pertains and a reference fluorescence value which pertains to the lowest among the physical parameter values of the second series higher than the physical parameter value to which the reference fluorescence value of the difference selected immediately before pertain.

By selecting the smallest in the group, the exemplary method may overcome distortions in the measured fluorescence values that cause similar fluorescence values to appear within a distance of values of the physical parameter, as described in further detail hereinbelow.

Figure 2:
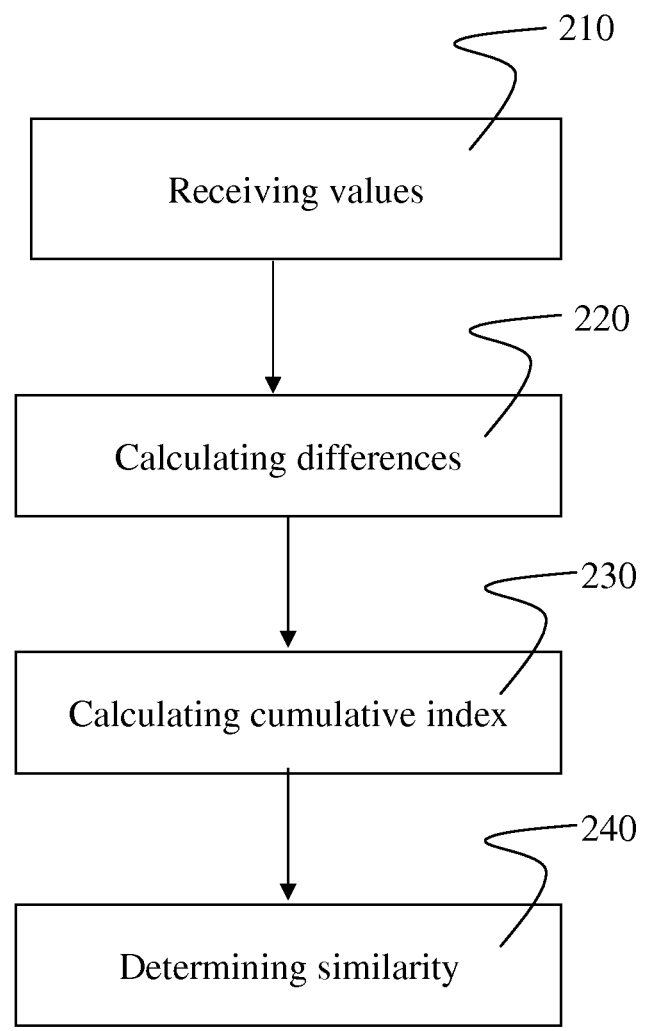

Reference is now made to FIG. 2, which is a simplified flowchart schematically illustrating a first method for cumulative differential chemical assay identification, according to an exemplary embodiment of the present invention.

A first exemplary method, according to an exemplary embodiment of the present invention, may be implemented on a computer, using a computer program, using hardware, using a combination of a computer program and hardware, etc.

In the exemplary method, there are received 210 two or more fluorescence values measured during a chemical reaction (say QF-PCR) which involves a test sample, say a blood sample taken from a patient infected with a bacteria (or a virus) which needs to be identified, say using the value receiver 110, as described in further detail hereinabove.

Each one of the fluorescence values pertains to a respective one of a first series of physical parameter values (say to a specific temperature present in a PCR reaction chamber in which the chemical reaction occurs, when the specific fluorescence value is measured).

In one example, the fluorescence values are measured (say by a photometer), during a LATE-PCR reaction, during a DNA Melting process, or during another chemical reaction, run in a reaction chamber, as known in the art.

In the example, each specific one of the measured fluorescence values pertains to a respective temperature measured in the reaction chamber when the specific fluorescence value is measured in the chamber.

Then, there are calculated 220 two or more pairwise differences, say by the difference calculator 120, as described in further detail hereinabove.

Each calculated 220 difference is a difference between a respective one of the measured fluorescence values and a respective one of reference fluorescence values of a reference sample (say of a sample of known bacterial content, a virus known to bear a specific mutation, etc.).

Optionally, the reference fluorescence values are values measured during a previous run of the chemical reaction, which involves the reference sample, values known in the art and available from scientific databases or textbooks, values gathered in previous runs of the chemical reaction on samples known to contain a certain bacteria, etc.

Optionally, the reference sample is a calculated average sample. That is to say that each one of the reference fluorescence values is an average value calculated over fluorescence values measured in previous runs of the chemical reaction, for a same respective physical parameter value (say for a same temperature or pressure).

Each one of the reference fluorescence values pertains to a respective one of a second series of physical parameter values (say a specific temperature of the previous run of the reaction, a specific temperature in a textbook table which lists reference fluorescence values per temperature values, etc).

Preferably, the two series of physical parameter values are identical. That is to say that for each one of the measured fluorescence values, there exists a reference fluorescence value which pertains to a same physical parameter value (say to a same temperature or pressure).

The calculated 220 difference may an absolute difference calculated 220 by subtracting the measured fluorescence value from the reference fluorescence value (or vise versa), a geometrical distance calculated 220 between points that represent the two fluorescence values, or a difference calculated 220 using a specific formula, say a formula predefined by a user of the apparatus 1000, etc., as known in the art.

Optionally, the calculated 220 pairwise differences include all possible differences, where each of the differences is a difference between a respective one of the measured fluorescence values and a respective one of the reference fluorescence values. That is to say that if there are n measured fluorescence values for respective n physical parameter values, and m reference fluorescence values for respective m physical parameter values, then, there are calculated 220 m×n differences.

Alternatively, the number of the calculated 220 differences is limited according to a predefined criterion, and is thus lower than m×n.

In a first example, the criterion is that each of the calculated 220 pairwise differences is a difference between a reference fluorescence value and a measured fluorescence value that pertain to values of the physical parameter within a predefined difference from each other, as described in further detail hereinbelow.

In a second example, the criterion is that each of the calculated 220 pairwise differences is a difference between a reference fluorescence value and a measured fluorescence value within a predefined difference from each other, as described in further detail hereinbelow.

In a third example, the criterion is that each of the calculated 220 pairwise differences is a difference between a reference fluorescence value and a measured fluorescence value of a proportion within a predefined limit. That is to say that the ratio of the two fluorescence values is below a predefined limit, as described in further detail hereinbelow.

Next, there is calculated 230 a cumulative index, by selecting a first difference among the pairwise differences, and selecting and adding to the first difference two or more additional ones of the pairwise differences, thereby summing the selected differences, say by the cumulative index calculator 130, as described in further detail hereinabove.

Each one of the additional differences is selected, according to a proximity standard applied on each two differences selected in a sequence (i.e. one after the other), as described in further detail hereinbelow.

The proximity standard is based on proximity of physical parameter values and on difference size, as described in further detail hereinbelow.

Finally, there is determined 240 similarity between the test sample and the reference sample, using the calculated cumulative index, say by the similarity determiner 140, as described in further detail hereinabove.

In one example, there may be determined 240 that the two samples carry a similar genetic mutation when the calculated cumulative index is below a threshold predefined by a user, and that the two samples do not carry the same mutation when the index exceeds the predefined threshold.

In another example, there may be determined 240 that the two samples belong to a same class of samples, thus classifying the two samples into a common class.

In a first example, the proximity standard is that each selected difference added to the first difference is smallest in a respective group, as described in further detail hereinbelow.

The group consists of calculated ones of the following differences:

1) a difference between a measured fluorescence value which pertains to a highest among the physical parameter values of the first series lower than a physical parameter value to which a measured fluorescence value of a difference selected immediately before the added selected difference pertains, and a reference fluorescence value which pertains to a highest among the physical parameter values of the second series lower than a physical parameter value to which a reference fluorescence value of the difference selected immediately before pertains;

2) a difference between a measured fluorescence value which pertains to the highest among the physical parameter values of the first series lower than the physical parameter value to which the measured fluorescence value of the difference selected immediately before pertains, and a reference fluorescence value which pertains to the physical parameter value to which the reference fluorescence value of the difference selected immediately before pertains; and 3) a difference between a measured fluorescence value which pertains to the physical parameter value to which the measured fluorescence value of the difference selected immediately before pertains, and a reference fluorescence value which pertains to the highest among the physical parameter values of the second series lower than the physical parameter value to which the reference fluorescence value of the difference selected immediately before pertains.

In a second example, the proximity standard remains that each selected difference added to the first difference is smallest in a respective group.

However, the group rather consists of calculated ones of following differences:

1) a difference between a measured fluorescence value which pertains to a lowest among the physical parameter values of the first series higher than a physical parameter value to which a measured fluorescence value of a difference selected immediately before the added selected difference pertains, and a reference fluorescence value which pertains to a lowest among the physical parameter values of the second series higher than a physical parameter value to which a reference fluorescence value of the difference selected immediately before pertains;

2) a difference between a measured fluorescence value which pertains to the lowest among the physical parameter values of the first series higher than the physical parameter value to which the measured fluorescence value of the difference selected immediately before pertains, and a reference fluorescence value which pertains to the physical parameter value to which the reference fluorescence value of the difference selected immediately before pertains; and 3) a difference between a measured fluorescence value which pertains to the physical parameter value to which the measured fluorescence value of the difference selected immediately before pertains and a reference fluorescence value which pertains to the lowest among the physical parameter values of the second series higher than the physical parameter value to which the reference fluorescence value of the difference selected immediately before pertain.

By selecting the smallest in the group, the exemplary method may overcome distortions in the measured fluorescence values that cause similar fluorescence values to appear within a distance of values of the physical parameter, as described in further detail hereinbelow.

Figure 3:
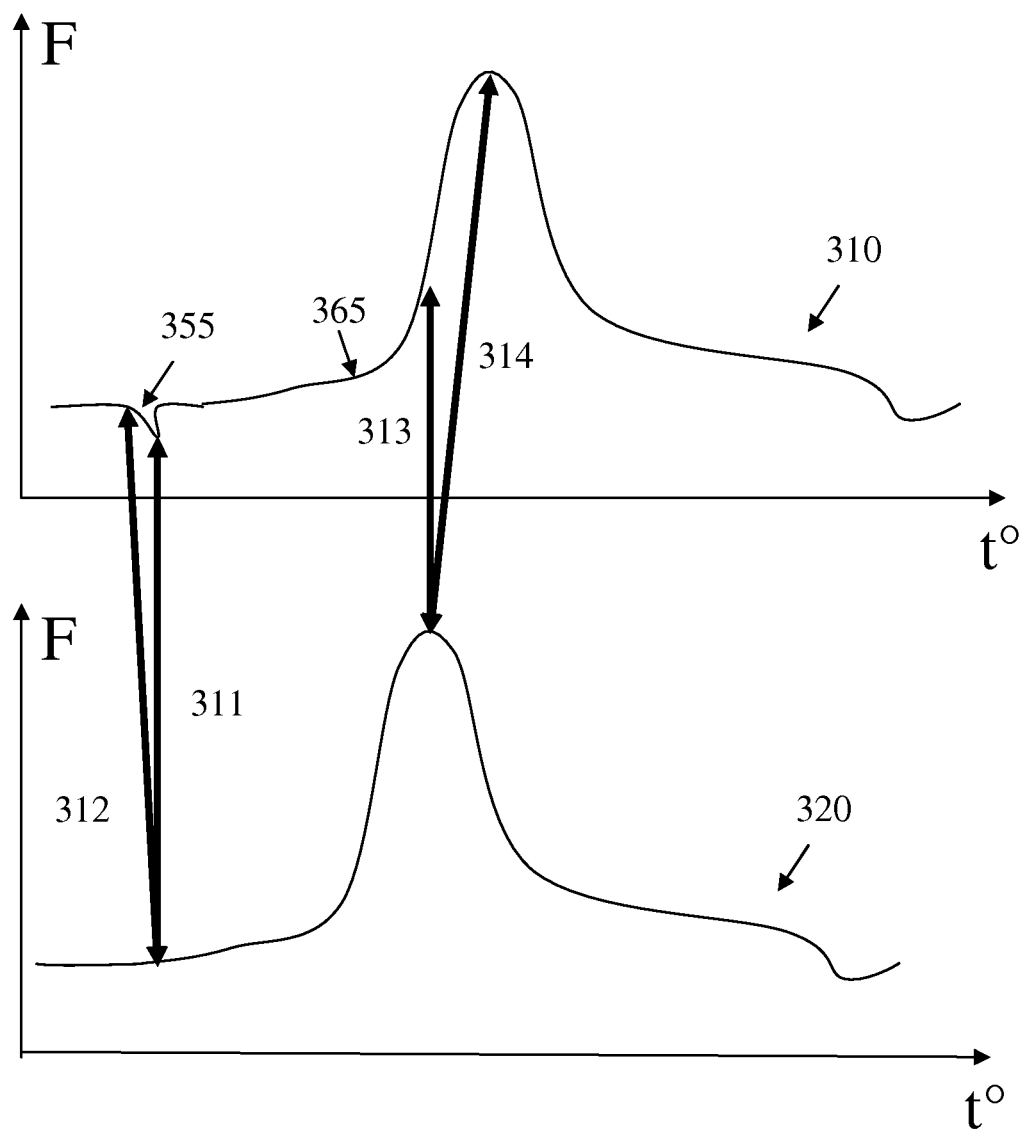

Reference is now made to FIG. 3, which is a simplified diagram schematically illustrating an exemplary proximity standard, according to an exemplary embodiment of the present invention.

According to an exemplary embodiment of the present invention, there is calculated a cumulative index. The cumulative index is calculated by selecting a first difference among the calculated pairwise differences, and selecting and adding to the first difference two or more additional pairwise differences, thereby summing the selected differences, as described in further detail hereinabove.

Each calculated difference is a difference between a respective one of the measured fluorescence values and a respective one of reference fluorescence values of a reference sample, as described in further detail hereinabove.

Each one of the additional differences is selected, according to a proximity standard applied on each two differences selected in a sequence (i.e. one after the other), as described in further detail hereinabove.

An exemplary proximity standard, illustrated in FIG. 3, is based on proximity of physical parameter values and on difference size.

In FIG. 3, a course of an exemplary chemical reaction (say QF-PCR) which involves a test sample is depicted as a first graph 310, and a course of a similar chemical reaction (say the QF-PCR reaction) which involves a reference sample similar in content to the test sample is depicted as a second graph 320.

Theoretically, the two chemical reaction courses, and thus the two graphs 310 and 320, are supposed to be the same, and to have a similar fluorescence value for each similar temperature (i.e. the physical parameter of FIG. 3), since the two samples are similar in content.

However, sensor variation, electrical noise, different ion compositions of analytes, delayed responses by a controller or a processor, and other factors, may introduce distortions into the measured fluorescence values, as described in further detail hereinabove.

Consequently, similar fluorescence values may be somewhat distanced. That is to say that the similar fluorescence values may appear for different temperature values (i.e. in displacement) rather than for a very same temperature value. Thus, the first graph 310 is slightly distorted in comparison with the second graph 320.

According to the exemplary proximity standard, instead of adding to the sum of differences, difference 311 which corresponds to fluorescence values of a same temperature value, there is added, difference 312 which corresponds to fluorescence values of different (though proximate) temperature values and is smaller than difference 311.

The selection of difference 312 over difference 311 compensates for a deletion 355 of a small part of the first graph 310, say due to temporary electrical interference during the chemical reaction which involves the test sample.

Similarly, according to the exemplary proximity standard, instead of adding to the sum of differences, difference 313 which corresponds to fluorescence values of a same temperature value, there is added, difference 314 which corresponds to fluorescence values of different (though proximate) temperature values and is smaller than difference 311.

The selection of difference 314 over difference 313 compensates for an insertion of a small segment 365 into the first graph 310, say due to a delayed response of a photometer used to measure the fluorescence values during the reaction which involves the test sample.

Figure 4:
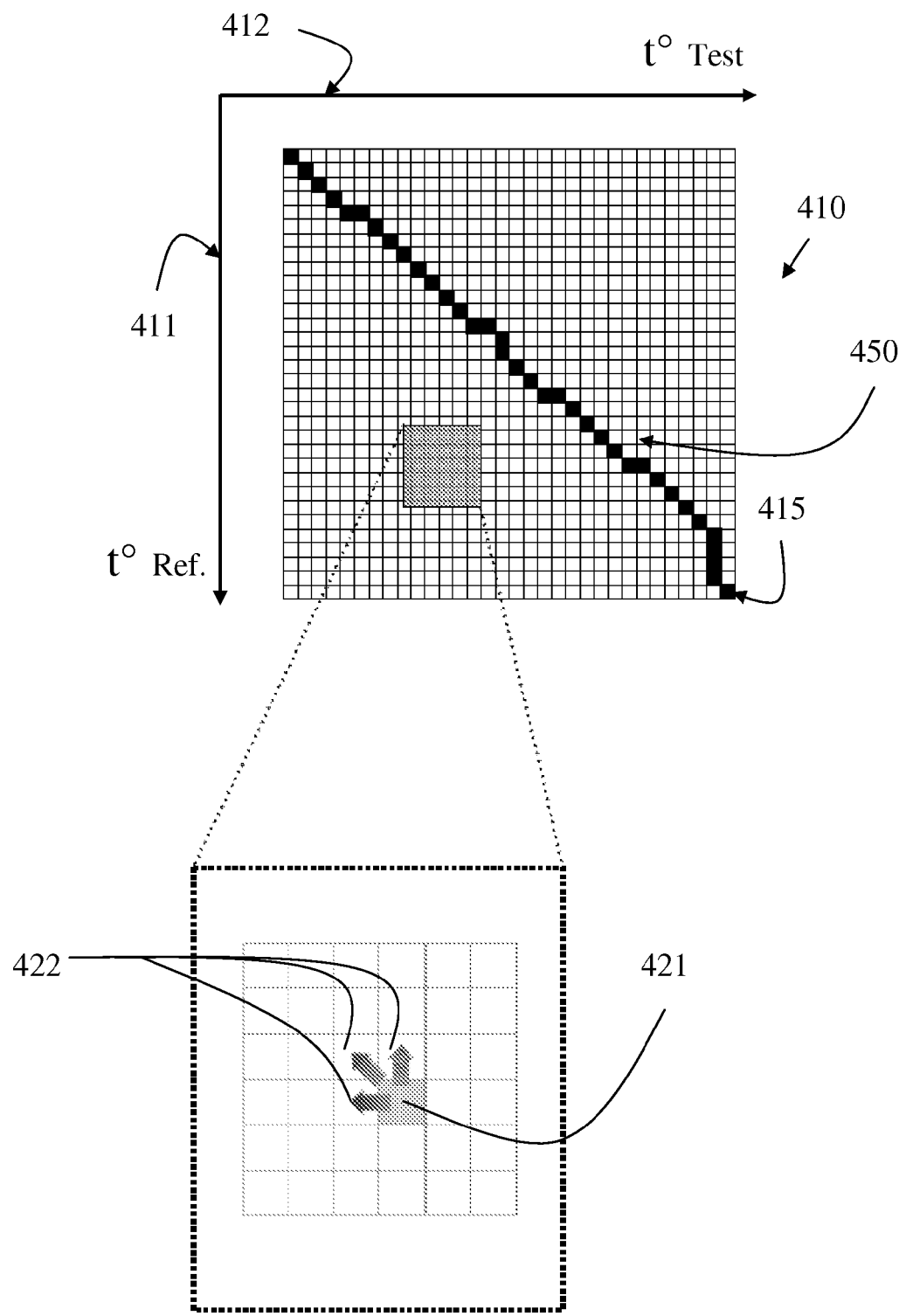

Reference is now made to FIG. 4, which is a simplified diagram schematically illustrating summing of differences, according to an exemplary embodiment of the present invention.

In one exemplary embodiment of the present invention, differences are calculated between measured fluorescence values of a test sample, and references fluorescence values of a reference sample, say using the difference calculator 120, as described in further detail hereinabove.

The calculated differences are placed in a matrix 410 sized m on n.

That is to say that the matrix 410 has two dimensions.

A first dimension 411 sized m corresponds to physical parameter values (say temperature values) of the reference sample, for the chemical reaction, as described in further detail hereinabove.

A second dimension 412 sized n corresponds to physical parameter values (say temperature values) of the test sample, for the chemical reaction, as described in further detail hereinabove.

Each cell of the matrix is indexed with specific i, j physical parameter values.

In one example, i denotes a temperature value which corresponds to a respective reference fluorescence value of the reference sample, whereas j denotes a temperature value which corresponds to a respective measured fluorescence value of the test sample, as described in further detail and illustrated using FIG. 6, hereinbelow.

The cell holds a difference calculated between the reference fluorescence value and the measured fluorescence value, of the respective i, j temperature values. The matrix 410 resembles matrices used in dynamic time wrapping methods employed for speech recognition processes, as known in the art.

In an exemplary method, according to an exemplary embodiment of the present invention, differences held in the matrix 410 cells are selected and summed, starting from the left corner cell 415, as described in further detail and illustrated using FIG. 6, hereinbelow.

Each difference selected and added to the difference in cell 415, is a smallest one in a respective group which consists of differences that occupy matrix 410 cells 422 adjacent to a cell 421 occupied by a difference selected immediately before the smallest difference in the group, as described in further detail hereinbelow.

Together, the selected differences occupy cells that form an optimal path 450, from one side of the matrix 410 to an opposite side of the matrix 410.

The sum of the differences selected and summed, is used as the cumulative index, for determining if the test sample and the reference sample are similar, as described in further detail hereinbelow.

In one example, there may determined that the two samples carry a similar genetic mutation when the calculated cumulative index is below a threshold (say a threshold predefined by a user of the apparatus 1000), and that the two samples do not carry a similar mutation when the index exceeds the threshold.

Unlike conventional comparisons, with the present embodiments, the comparisons between a series of measured fluorescence values of a test sample, and as series of reference fluorescence values of a reference sample, give weight to both magnitude of changes, and number of changes. The path 450 defined by the differences added in a sum, gives weight to both the magnitude of changes, and the number of changes, between the two series.

Figure 5A:
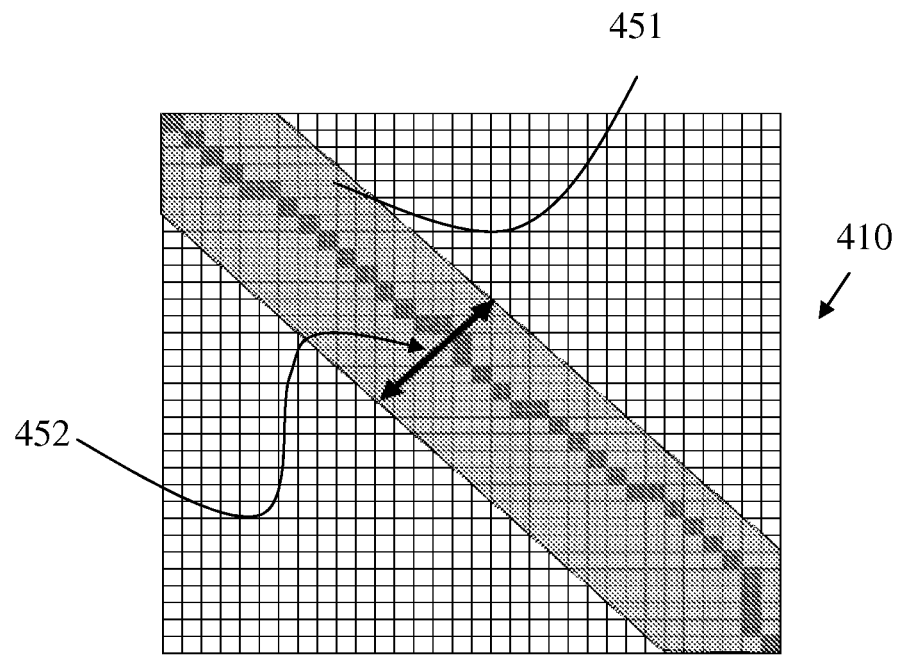

Reference is now made to FIG. 5A, which is a first simplified diagram schematically illustrating summing of differences within predefined boundaries, according to an exemplary embodiment of the present invention.

According to an exemplary embodiment of the present invention, the differences calculated (say by the difference calculator 120 of apparatus 1000) are limited according to a predefined criterion. Consequently, there may be avoided calculation of differences of extreme values (i.e. outliers) that may prove contra-productive, when added in a sum, for calculating the cumulative index.

For example, the criterion may be that each of the calculated pairwise differences is a difference between a reference fluorescence value and a measured fluorescence value that pertain to values of the physical parameter (say the temperature values) within a predefined difference from each other, as described in further detail and illustrated using FIG. 7, hereinbelow.

Consequently, the selected differences occupy cells of the matrix 410 that are limited to a partial area of the matrix 410, say to a longitudinal band 451 of a specific width 452, to an area shaped like a parallelogram of specific dimensions (not shown), etc.

Figure 5B:
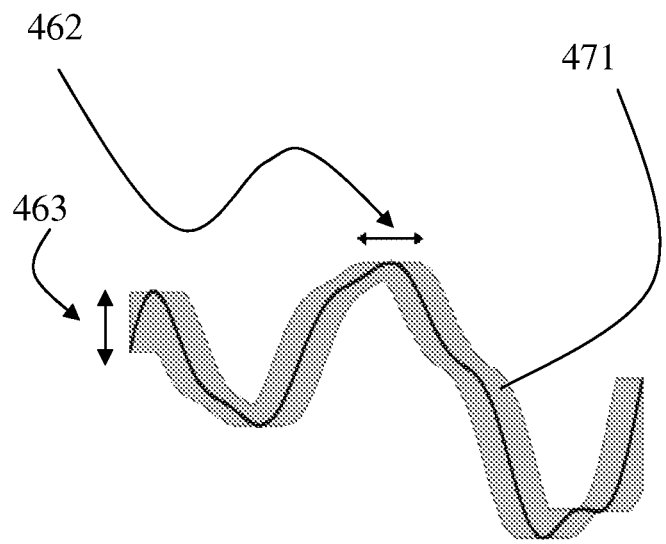

Reference is now made to FIG. 5B, which is a second simplified diagram schematically illustrating summing of differences within predefined boundaries, according to an exemplary embodiment of the present invention.

In one exemplary embodiment, the calculated differences are limited to pairs of fluorescence values that pertain to values of the physical parameter (say the temperature values) within a predefined limit 462 (i.e. difference) from each other.

A further limitation imposed on the calculated differences of the example, may be that the pair of fluorescence values' ratio must not exceed a predefined ratio limit 463.

The two limits may be imposed using LCSS (Longest Common Subsequences) techniques, as known in the art.

The limits 462, 463, may be defined by a user of apparatus 1000, say using a dedicated GUI (Graphical User Interface).

The selected differences occupy cells of the matrix 410 that are limited to a partial area 471 of the matrix 410.

Consequently, there may be avoided calculation of differences of extreme values (i.e. outliers) that may prove contra-productive, when added in a sum, for calculating the cumulative index.

Figure 6:
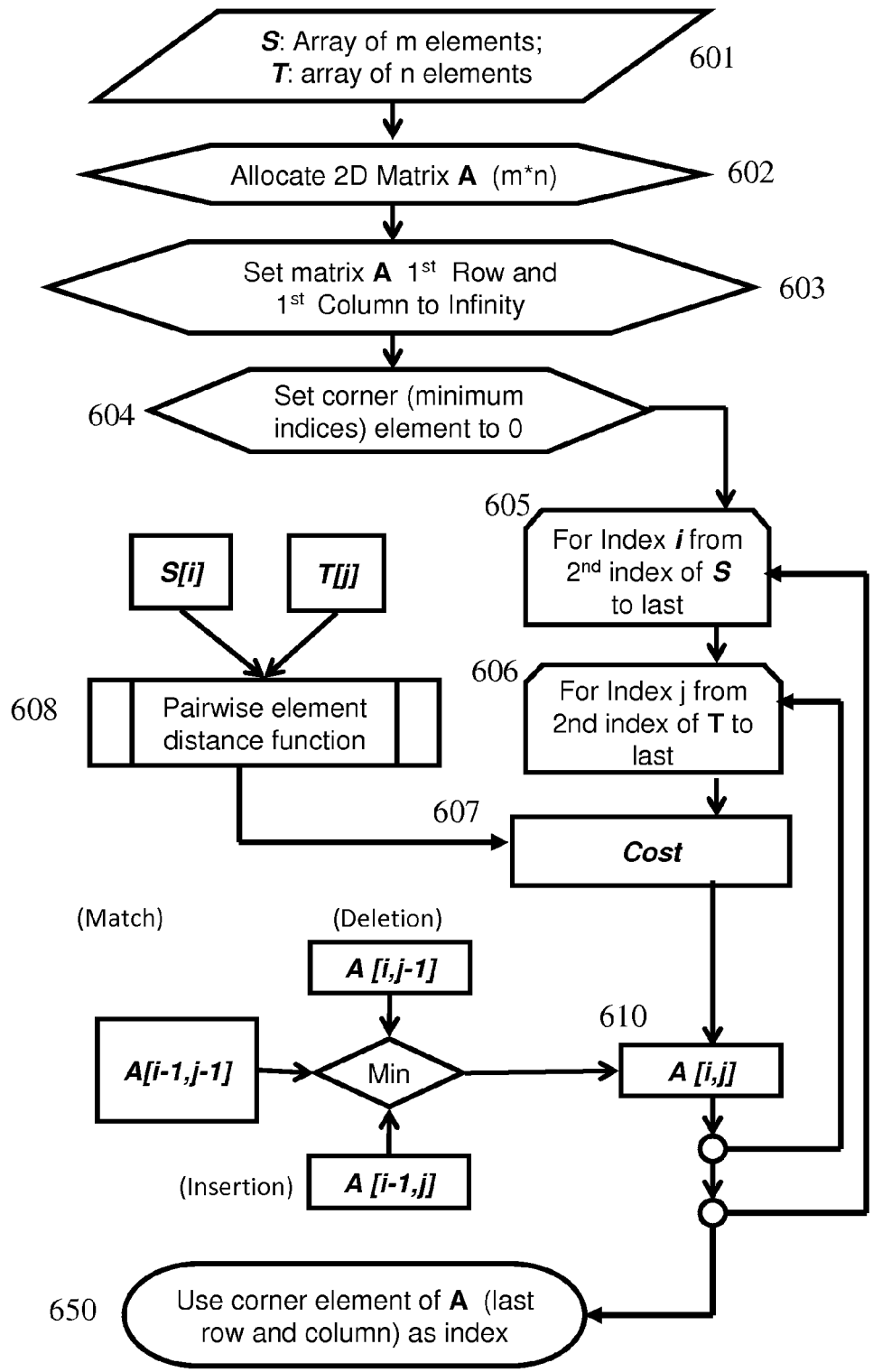

Reference is now made to FIG. 6, which is a simplified flowchart schematically illustrating a second method for cumulative differential chemical assay identification, according to an exemplary embodiment of the present invention.

A second exemplary method, according to an exemplary embodiment of the present invention, may be implemented on a computer, using a computer program, using hardware, using a combination of a computer program and hardware, etc.

In the exemplary method, there is received 601 an array (denoted T) of n (two or more elements. Each of the n elements is a fluorescence value measured during a chemical reaction which involves a test sample, say a blood sample taken from a patient infected with a bacteria (or a virus) which needs to be identified.

Each one of the measured fluorescence values pertains to a respective one of a first series of n physical parameter values, say to a specific temperature present in a PCR reaction chamber in which the chemical reaction occurs, when the specific fluorescence value is measured.

In a first exemplary implementation of the second method, fluorescence values are measured per each single unit of temperature rise, starting from a standard temperature at which the reaction or a phase of the reaction, is believed to begin, and ending at a standard temperature at which the reaction or phase is believed to end. The standard temperatures may be specific to the reaction in general, to a device, to a laboratory, etc., or to any combination thereof.

For example, if the reaction is believed to begin at a standard temperature of 23° C. and to end at a standard temperature of 60° C., a first one of the fluorescence values may be measured when the temperature is 24° C., a second fluorescence values may be measured when the temperature rises to 25° C., a second fluorescence values may be measured when the temperature rises to 26° C., etc., and so on, in steps of one degree, until the temperature rises to 60° C., or starts to decline.

In the first exemplary implementation, n denotes both the index of the measured fluorescence value in T and the temperature rise over the standard starting temperature, for the test sample.

Further received 601 in the exemplary method, is an array (denoted S) of m (two or more) elements. Each of the m elements is a reference fluorescence value of a similar chemical reaction which involves a reference sample (typically of known content), as described in further detail hereinabove. The reference fluorescence value pertains to a respective one of a second series of physical parameter values, say to a specific temperature.

The second series of reference fluorescence values include values measured during a previous run of the chemical reaction, starting at 23° C. and ending at 60° C. (or at a lower temperature).

Further in the first exemplary implementation, m denotes both the index of the measured fluorescence value in S and the temperature rise over the standard starting temperature, for the reference sample.

Then, there is allocated 602 a two dimensional matrix A sized m on n, say matrix 410, as described in further detail hereinabove.

Next, all elements in matrix A's first row and first column are set 603 to infinity (or simply to a value higher than any fluorescence value expected to be measured or used as a reference value), and a corner element of the matrix (i.e. an element of lowest indices) is set 604 to zero.

Then, looping 605 with an index i of values from S' second index to last, and for each value of i, inner-looping 606 with an index j of values from T's second index to last, there is calculated a sum, for each inner-looping cycle.

The sum is calculated by calculating a cost 607 which is a difference 608 between S[i] (i.e. a reference fluorescence value of a temperature 23°+i) and T[j] (i.e. a measured fluorescence value of temperature 23°+j), and adding to the cost 607, a smallest member of a group of neighboring cells of the matrix A. The group consists of cells A [i,j−1], A[i−1,j−1] and A [i−1,j].

A [ij] 610 is set to the calculated sum.

A [i,j−1] is the smallest of the three in case of a value deletion in the measured fluorescence values compared with the reference measured fluorescence values, A [i−1,j] is the smallest of the three in case of a value insertion in the measured fluorescence values compared with the reference measured fluorescence values, and A[i−1,j−1] is the smallest when there is neither a deletion nor an insertion.

Finally, the corner element (i.e. last element in row and column) is used 650 as the cumulative index, for determining if the test sample is similar to the reference sample, as described in further detail hereinabove.

In a second implementation of the second method, the fluorescence values of array T are values measured per each single unit of temperature decline, starting from a standard starting temperature at which the decline in the temperature is expected to begin, and ending at a standard target temperature. The standard temperatures may be specific to the reaction in general, to a device, to a laboratory, etc., or to any combination thereof.

Further in the second exemplary implementation, the fluorescence values of array S are values that pertain to each single unit of temperature decline, starting from a standard starting temperature at which the decline in the temperature is expected to begin, and ending at a standard target temperature. The standard temperatures may be specific to the reaction in general, to a device, to a laboratory, etc., or to any combination thereof.

Consequently, in the second implementation, n denotes both the index of the measured fluorescence value in T and the temperature decline for the test sample and m denotes both the index of the reference fluorescence value in S and the temperature decline for the standard sample. With an example standard starting temperature of 60°, S[i] denotes a reference fluorescence value which pertains to a temperature 60°−i and T[j] denotes a measured fluorescence value which pertains to a temperature 60°−j.

Figure 7:
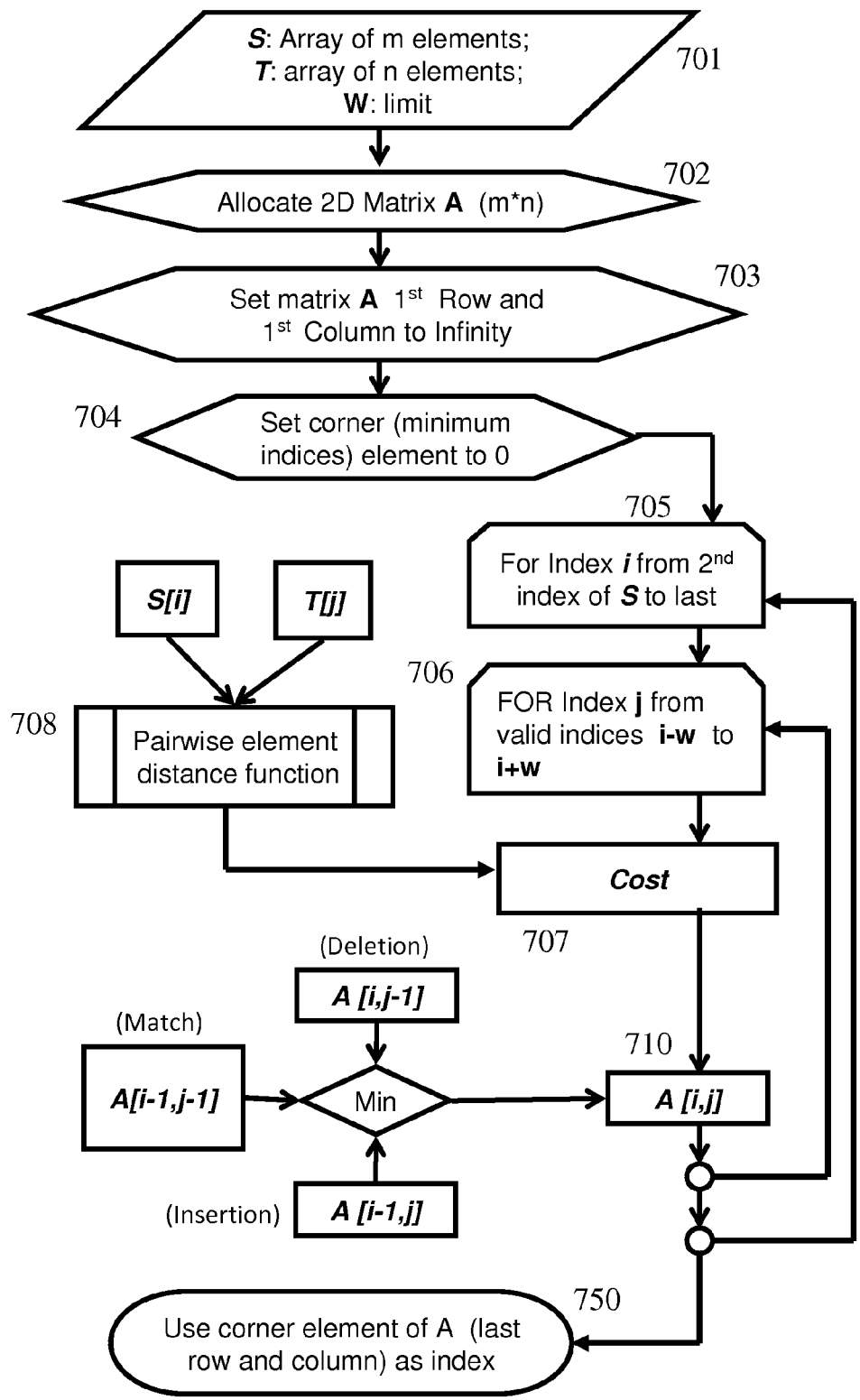

Reference is now made to FIG. 7, which is a simplified flowchart schematically illustrating a third method for cumulative differential chemical assay identification, according to an exemplary embodiment of the present invention.

A third exemplary method, according to an exemplary embodiment of the present invention, may be implemented on a computer, using a computer program, using hardware, using a combination of a computer program and hardware, etc.

In the exemplary method, there is received 701 an array (denoted T) of n (two or more) elements. Each of the n element is a fluorescence value measured during a chemical reaction which involves a test sample, say a blood sample taken from a patient infected with a bacteria (or a virus) which needs to be identified.

Each one of the measured fluorescence values pertains to a respective one of a first series of n physical parameter values, say to a specific temperature present in a PCR reaction chamber in which the chemical reaction occurs, when the specific fluorescence value is measured.

In a first exemplary implementation of the second method, fluorescence values are measured per each single unit of temperature rise, starting from a standard temperature at which the reaction or a phase of the reaction, is believed to begin, and ending at a standard temperature at which the reaction or phase is believed to end. The standard temperatures may be specific to the reaction in general, to a device, to a laboratory, etc., or to any combination thereof.

For example, if the reaction begins at a standard temperature of 23° C. and ends at a standard temperature of 60° C., a first one of the fluorescence values may be measured when the temperature is 24° C., the second fluorescence values may be measured when the temperature rises to 25° C., the second fluorescence values may be measured when temperature rises to 26° C., etc., and so on, in steps of one degree, until the temperature rises to 60° C., or starts to decline.

In the first exemplary implementation, n denotes both the index of the measured fluorescence value in T and the temperature rise over the standard starting temperature, for the test sample.

Further received 701 in the third exemplary method, is an array (denoted S) of m (two or more) elements. Each of the m elements is a reference fluorescence value of a similar chemical reaction which involves a reference sample (typically of known content), as described in further detail hereinabove. The reference fluorescence value pertains to a respective one of a second series of physical parameter values, say to a specific temperature.

The second series of reference fluorescence values include values measured during a previous run of the chemical reaction, starting at 23° C., with steps of one degree, and ending at 60° C. (or at a lower temperature).

Further in the first exemplary implementation, m denotes both the index of the measured fluorescence value in S and the temperature rise over the standard starting temperature, for the reference sample.

Further received 701 is a limit (denoted w) to be imposed on differences, such that a difference may be calculated only between a measured fluorescence value and a reference fluorescence value that pertain to temperature values within a difference not greater than w from each other.

Then, there is allocated 702 a two dimensional matrix A sized m on n, say matrix 410, as described in further detail hereinabove.

Next, all elements in the matrix A's first row and first column are set 703 to infinity (or simply to a value higher than any fluorescence value expected to be measured or used as a reference value), and a corner element of the matrix (i.e. an element of lowest indices) is set 704 to zero.

Then, looping 705 with an index i of values from S' second index to last, and for each value of i, inner-looping 706 with an index j of valid values from i−w to i+w, there is calculated a sum, for each inner-looping cycle.

The sum is calculated by calculating a cost 707 which is a difference 708 between S[i] (i.e. a reference fluorescence value of temperature 23°+i) and T[j] (i.e. a measured fluorescence value of temperature 23°+j), and adding to the cost 707, a smallest member of a group of neighboring cells of the matrix A. The group consists of cells A [ij−1], A[i−1,j−1] and A [i−1,j].

A [i,j] 710 is set to the calculated sum.

A [i,j−1] is the smallest of the three in case of a value deletion in the measured fluorescence values compared with the reference measured fluorescence values, A [i−1,j] is the smallest of the three in case of a value insertion in the measured fluorescence values compared with the reference measured fluorescence values, and A[i−1,j−1] is the smallest of the three when there is neither a deletion nor an insertion.

Finally, the corner element (i.e. last element in row and column) is used 750 as the cumulative index, for determining if the test sample is similar to the reference sample, as described in further detail hereinabove.

In a second implementation of the second method, the fluorescence values of array T are values measured per each single unit of temperature decline, starting from a standard starting temperature at which the decline in the temperature is expected to begin, and ending at a standard target temperature. The standard temperatures may be specific to the reaction in general, to a device, to a laboratory, etc., or to any combination thereof.

Further in the second exemplary implementation, the fluorescence values of array S are values that pertain to each single unit of temperature decline, starting from a standard starting temperature at which the decline in the temperature is expected to begin, and ending at a standard target temperature. The standard temperatures may be specific to the reaction in general, to a device, to a laboratory, etc., or to any combination thereof.

Consequently, in the second implementation, n denotes both the index of the measured fluorescence value in T and the temperature decline for the test sample and m denotes both the index of the reference fluorescence value in S and the temperature decline for the standard sample. With an example standard starting temperature of 60°, S[i] denotes a reference fluorescence value which pertains to a temperature 60°−i and T[j] denotes a measured fluorescence value which pertains to a temperature 60°−j.

Figure 8:
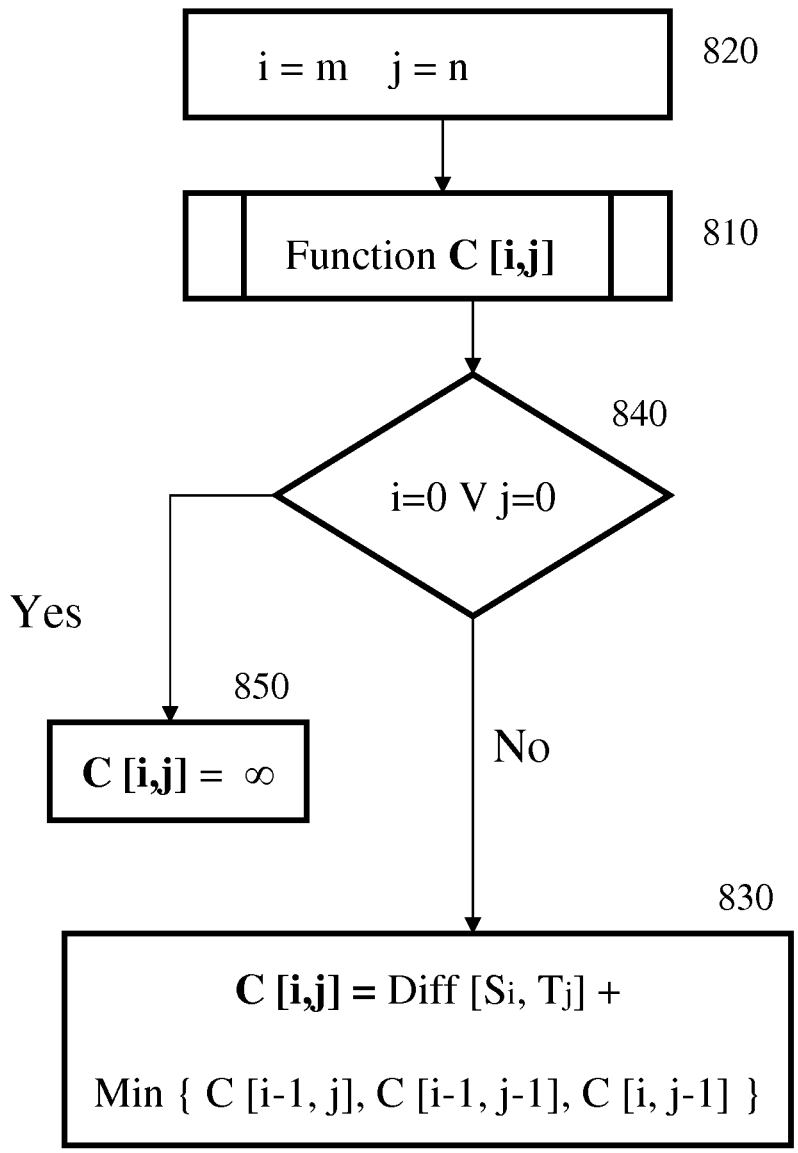

Reference is now made to FIG. 8, which is a simplified flowchart schematically illustrating a fourth method for cumulative differential chemical assay identification, according to an exemplary embodiment of the present invention.

A fourth exemplary method, according to exemplary embodiments of the present invention, is a recursive method which may be implemented using a recursive computer program, as known in the art.

In the fourth exemplary method, there may be carried out a recursive set of steps, which involves recursive iterations for values of a recursive computer function C [i, j] 810, with the above described indices i and j initially set 820 to the m and n values, respectively. A recursive computer function is computer function which is allowed to call itself, as known in the art.

i and j also denote the temperature change, be the change a temperature rise or a temperature decline, as described in further detail, and illustrate using FIGS. 6 and 7 hereinabove.

Then, per each iteration of the recursive method, the value of C[i, j] is set 830 to a sum of the calculated difference between the respective measured fluorescence value and reference fluorescence value, and the smallest of a group which consists of C[i−1, j], C[i, j−1] and C[i−1, j−1]. That is to say that the recursive function C [i, j] 810 is called for each of the three members of the group.

The iterations continue until at least one of the indices i, j reaches zero.

When one of the indices i, j reaches zero 840, C[i, j] is set 850 to infinity (or a to a value higher than any fluorescence value expected to be measured or used as a reference value), and the recursive computer function C[i, j] 810 stops calling itself.

It is expected that during the life of this patent many relevant devices and systems will be developed and the scope of the terms herein, particularly of the terms "PCR", "LATE-PCR" and "QF-PCR", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for correcting distortion in measurement of fluorescence values using at least one sensor during a chemical reaction that is used for determining similarity between a test sample and a reference sample, the apparatus comprising:
   at least one computer;
   a value receiver, implemented on one of said at least one computer, configured to receive a plurality of fluorescence values measured by the at least one sensor during the chemical reaction, each one of the measured fluorescence values pertaining to a respective one of a first series of physical parameter values, and to receive a plurality of reference fluorescence values of the reference sample, each one of the reference fluorescence values pertaining to a respective one of a second series of physical parameter values;
   a difference calculator, implemented on one of said at least one computer, in communicated with said value receiver, configured to calculate a plurality of pairwise differences, each difference being between a respective one of the received measured fluorescence values and a respective one of the received reference fluorescence values;
   a cumulative index calculator, implemented on one of said at least one computer, in communicated with said difference calculator, configured to calculate an index by selecting a first difference among said calculated pairwise differences, and selecting and adding to said first difference a plurality of ones of said pairwise differences, each one of the added differences being selected according to a proximity standard applied on each two differences selected in a sequence, the proximity standard being based on proximity of physical parameter values and on difference size; and
   a similarity determiner, implemented on one of said at least one computer, in communicated with said cumulative index calculator, configured to determine similarity between said test sample and said reference sample, using said calculated index,
   wherein said proximity standard is that each selected difference added to the first difference is smallest in a respective group consisting of calculated ones of: a difference between a measured fluorescence value pertaining to a highest among said physical parameter values of said first series lower than a physical parameter value to which a measured fluorescence value of a difference selected immediately before said added selected difference pertains and a reference fluorescence value pertaining to a highest among said physical parameter values of said second series lower than a physical parameter value to which a reference fluorescence value of said difference selected immediately before pertains, a difference between a measured fluorescence value pertaining to said highest among said physical parameter values of said first series lower than said physical parameter value to which said measured fluorescence value of said difference selected immediately before pertains and a reference fluorescence value pertaining to said physical parameter value to which said reference fluorescence value of said difference selected immediately before pertains, and a difference between a measured fluorescence value pertaining to said physical parameter value to which said measured fluorescence value of said difference selected immediately before pertains and a reference fluorescence value pertaining to said highest among said physical parameter values of said second series lower than said physical parameter value to which said reference fluorescence value of said difference selected immediately before pertains, and wherein said cumulative index calculator calculates the index by selecting the added differences according to said proximity standard applied on each two differences selected in a sequence, thereby correcting the distortion in the measurement of the fluorescence values using the at least one sensor during the chemical reaction.

2. The apparatus of claim 1, wherein the two series of the physical parameter values are identical.

3. The apparatus of claim 1, wherein said physical parameter is temperature.

4. The apparatus of claim 1, wherein said chemical reaction is a Linear After The Exponential (LATE) Polymerase Chain Reaction (PCR).

5. The apparatus of claim 1, wherein said chemical reaction is DNA Melting.

6. The apparatus of claim 1, wherein each of said calculated pairwise differences is a difference between a reference fluorescence value and a measured fluorescence value pertaining to values of said physical parameter within a predefined difference from each other.

7. The apparatus of claim 1, wherein each of said calculated pairwise differences is a difference between a reference fluorescence value and a measured fluorescence value within a predefined difference from each other.

8. The apparatus of claim 1, wherein each of said calculated pairwise differences is a difference between a reference fluorescence value and a measured fluorescence value having a ratio below a predefined limit.

9. A computer implemented method for correcting distortion in measurement of fluorescence values using at least one sensor during a chemical reaction that is used for determining similarity between a test sample and a reference sample, the method comprising:
   a) receiving a plurality of fluorescence values measured by the at least one sensor during the chemical reaction, each one of the measured fluorescence values pertaining to a respective one of a first series of physical parameter values, and receiving a plurality of reference fluorescence values of the reference sample, each one of the reference fluorescence values pertaining to a respective one of a second series of physical parameter values;
   b) calculating a plurality of pairwise differences, each difference being between a respective one of the received measured fluorescence values and a respective one of the received reference fluorescence values;
   c) calculating an index by selecting a first difference among said calculated pairwise differences, and selecting and adding to said first difference a plurality of ones of said pairwise differences, each one of the added differences being selected according to a proximity standard applied on each two differences selected in a sequence, the proximity standard being based on proximity of physical parameter values and on difference size; and d) determining similarity between said test sample and said reference sample, using said calculated index, wherein said proximity standard is that each selected difference added to the first difference is smallest in a respective group consisting of calculated ones of: a difference between a measured fluorescence value pertaining to a highest among said physical parameter values of said first series lower than a physical parameter value to which a measured fluorescence value of a difference selected immediately before said added selected difference pertains and a reference fluorescence value pertaining to a highest among said physical parameter values of said second series lower than a physical parameter value to which a reference fluorescence value of said difference selected immediately before pertains, a difference between a measured fluorescence value pertaining to said highest among said physical parameter values of said first series lower than said physical parameter value to which said measured fluorescence value of said difference selected immediately before pertains and a reference fluorescence value pertaining to said physical parameter value to which said reference fluorescence value of said difference selected immediately before pertains, and a difference between a measured fluorescence value pertaining to said physical parameter value to which said measured fluorescence value of said difference selected immediately before pertains and a reference fluorescence value pertaining to said highest among said physical parameter values of said second series lower than said physical parameter value to which said reference fluorescence value of said difference selected immediately before pertains, and wherein step c) calculates the index by selecting the added differences according to said proximity standard applied on each two differences selected in a sequence, thereby correcting the distortion in the measurement of the fluorescence values using the at least one sensor during the chemical reaction.

10. The method of claim 9, wherein the two series of the physical parameter values are identical.

11. The method of claim 9, wherein said physical parameter is temperature.

12. The method of claim 9, wherein said chemical reaction is a Linear After The Exponential (LATE) Polymerase Chain Reaction (PCR).

13. The method of claim 9, wherein said chemical reaction is DNA Melting.

14. The method of claim 9, wherein each of said calculated pairwise differences is a difference between a reference fluorescence value and a measured fluorescence value pertaining to values of said physical parameter within a predefined difference from each other.

15. The method of claim 9, wherein each of said calculated pairwise differences is a difference between a reference fluorescence value and a measured fluorescence value within a predefined difference from each other.

16. The method of claim 9, wherein each of said calculated pairwise differences is a difference between a reference fluorescence value and a measured fluorescence value having a ratio below a predefined limit.

17. An apparatus for correcting distortion in measurement of fluorescence values using at least one sensor during a chemical reaction that is used for determining similarity between a test sample and a reference sample, comprising:

at least one computer, a value receiver, implemented on one of said at least one computer, configured to receive a plurality of fluorescence values measured by the at least one sensor during the chemical reaction, each one of the measured fluorescence values pertaining to a respective one of a first series of physical parameter values, and receive a plurality of reference fluorescence values of the reference sample, each one of the reference fluorescence values pertaining to a respective one of a second series of physical parameter values;

a difference calculator, implemented on one of said at least one computer, in communicated with said value receiver, configured to calculate a plurality of pairwise differences, each difference being between a respective one of the received measured fluorescence values and a respective one of the received reference fluorescence values;

a cumulative index calculator, implemented on one of said at least one computer, in communicated with said difference calculator, configured to calculate an index by selecting a first difference among said calculated pairwise differences, and selecting and adding to said first difference a plurality of ones of said pairwise differences, each one of the added differences being selected according to a proximity standard applied on each two differences selected in a sequence, the proximity standard being based on proximity of physical parameter values and on difference size; and a similarity determiner, implemented on one of said at least one computer, in communicated with said cumulative index calculator, configured to determine similarity between said test sample and said reference sample, using said calculated index, wherein said proximity standard is that each selected difference added to the first difference is smallest in a respective group consisting of calculated ones of: a difference between a measured fluorescence value pertaining to a lowest among said physical parameter values of said first series higher than a physical parameter value to which a measured fluorescence value of a difference selected immediately before said added selected difference pertains and a reference fluorescence value pertaining to a lowest among said physical parameter values of said second series higher than a physical parameter value to which a reference fluorescence value of said difference selected immediately before pertains, a difference between a measured fluorescence value pertaining to said lowest among said physical parameter values of said first series higher than said physical parameter value to which said measured fluorescence value of said difference selected immediately before pertains and a reference fluorescence value pertaining to said physical parameter value to which said reference fluorescence value of said difference selected immediately before pertains, and a difference between a measured fluorescence value pertaining to said physical parameter value to which said measured fluorescence value of said difference selected immediately before pertains and a reference fluorescence value pertaining to said lowest among said physical parameter values of said second series higher than said physical parameter value to which said reference fluorescence value of said difference selected immediately before pertains, and wherein said cumulative index calculator calculates the index by selecting the added differences according to said proximity standard applied on each two differences selected in a sequence, thereby correcting the distortion in the measurement of the fluorescence values using the at least one sensor during the chemical reaction.

18. A computer implemented method for correcting distortion in measurement of fluorescence values using at least one sensor during a chemical reaction that is used for determining similarity between a test sample and a reference sample, comprising:
   a) receiving a plurality of fluorescence values measured by the at least one sensor during the chemical reaction, each one of the measured fluorescence values pertaining to a respective one of a first series of physical parameter values, and receiving a plurality of reference fluorescence values of the reference sample, each one of the reference fluorescence values pertaining to a respective one of a second series of physical parameter values;
   b) calculating a plurality of pairwise differences, each difference being between a respective one of the received measured fluorescence values and a respective one of the received reference fluorescence values;
   c) calculating an index by selecting a first difference among said calculated pairwise differences, and selecting and adding to said first difference a plurality of ones of said pairwise differences, each one of the added differences being selected according to a proximity standard applied on each two differences selected in a sequence, the proximity standard being based on proximity of physical parameter values and on difference size; and
   d) determining similarity between said test sample and said reference sample, using said calculated index,
   wherein said proximity standard is that each selected difference added to the first difference is smallest in a respective group consisting of calculated ones of: a difference between a measured fluorescence value pertaining to a lowest among said physical parameter values of said first series higher than a physical parameter value to which a measured fluorescence value of a difference selected immediately before said added selected difference pertains and a reference fluorescence value pertaining to a lowest among said physical parameter values of said second series higher than a physical parameter value to which a reference fluorescence value of said difference selected immediately before pertains, a difference between a measured fluorescence value pertaining to said lowest among said physical parameter values of said first series higher than said physical parameter value to which said measured fluorescence value of said difference selected immediately before pertains and a reference fluorescence value pertaining to said physical parameter value to which said reference fluorescence value of said difference selected immediately before pertains, and a difference between a measured fluorescence value pertaining to said physical parameter value to which said measured fluorescence value of said difference selected immediately before pertains and a reference fluorescence value pertaining to said lowest among said physical parameter values of said second series higher than said physical parameter value to which said reference fluorescence value of said difference selected immediately before pertains, and
   wherein step c) calculates the index by selecting the added differences according to said proximity standard applied on each two differences selected in a sequence, thereby correcting the distortion in the measurement of the fluorescence values using the at least one sensor during the chemical reaction.

* * * * *